United States Patent [19]

Koreeda et al.

[11] Patent Number: 5,453,500
[45] Date of Patent: Sep. 26, 1995

[54] WATER-SOLUBLE GLYCOSYLATED DERIVATIVES OF 1,2-DITHIIN COMPOUNDS

[75] Inventors: Masato Koreeda; Brian K. Shull; Wu Yang, all of Ann Arbor, Mich.

[73] Assignee: The University of Michigan, Ann Arbor, Mich.

[21] Appl. No.: 249,492

[22] Filed: May 26, 1994

[51] Int. Cl.$^6$ .................. C07D 327/06; C07D 343/00; A61K 7/035; A61K 31/715
[52] U.S. Cl. .................. 536/123; 549/14; 536/124
[58] Field of Search .................. 536/123, 124; 514/436, 23, 53; 549/14

[56] References Cited

U.S. PATENT DOCUMENTS 5,202,348  4/1993  Towers .................. 514/436

OTHER PUBLICATIONS

Freeman, F. et al. Sulfur Reports 1989, 9, 207–246.
Cimiraglia, R. et al. J. Mol. Str. (Theochem) 1991, 230, 287–293.
Constabel, C. P.; Towers, G. H. N., Planta Medica 1989, 55, 35–37.
Towers, G. H. N.; Champagne, D. B. In Chemistry & Biology of Naturally–Occurring Acetylenes & Related Compounds (NOARC) ed by Lam, J. et al. Elsevier, Amsterdam, 1988, 139–149.
Schroth, W. et al Angew. Chem. Int. Ed. Engl. 1967, 6, 698–699.

Primary Examiner—Ronald W. Griffin
Attorney, Agent, or Firm—Young, MacFarlane & Wood

[57] ABSTRACT

Novel water-soluble mono and disaccharides of 1,2-dithiins, as well as methods for their synthesis and the synthesis of 3,6-bis(hydroxymethyl)-1,2-dithiin, are provided. The water-soluble compounds have useful medicinal applications, e.g., as an antifungal agent or antibacterial agent in a pharmaceutically acceptable carrier.

11 Claims, No Drawings

WATER-SOLUBLE GLYCOSYLATED DERIVATIVES OF 1,2-DITHIIN COMPOUNDS

FIELD OF THE INVENTION

The present invention relates to novel water-soluble glycosylated 1,2-dithiin derivatives having useful pharmacological properties, and to unique chemical methods for their synthesis from known dithiin compounds or their known precursors.

BACKGROUND OF THE INVENTION 1,2-Dithiacyclohexa-3,5-dienes, also referred to as 1,2-dithiins, are a class of compounds that have the 1,2-dithiabenzene ring 1 where two contiguous CH groups of the benzene ring

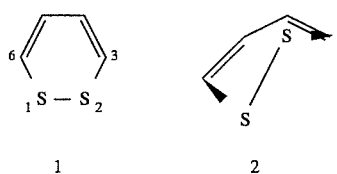

are replaced by two sulfur atoms. For this reason, considerable attention has been focused as to whether this heterocyclic system, being analogous to that of benzene, retains aromaticity (see, e.g., Aihara, *J. Bull.Chem. Soc. Jpn.* 1990, 63, 2899–2903; review: Freeman, F. et al. *Sulfur Reports* 1989, 9, 207–246). Results from spectroscopic and computational studies indicate that the heterocyclic ring is anti-aromatic and adopts a half-chair conformation 2 where the two sulfur atoms are placed above and below of the skewed (27.6°) diene moiety with twist angles of C=C—S and CS—SC being 122°and 54.2°, respectively (Borsdorf, R et al. *Tetrahedron* 1990, 26, 3227–3231; Cimiraglia, R. et al. *J.Mol.Str. (Theochem)* 1991,230,287–293). These anti-aromatic, 1,2-dithiin-containing compounds have also been found in nature (Freeman, F. et al. *Sulfur Reports* 1989, 9, 207–246). Nearly a dozen such natural products have been isolated primarily from the Asteraceae plants. It is also of considerable interest to note that all of these 1,2-dithiin natural products contain a multitude of acetylene groups. A number of naturally occurring 1,2-dithiin compounds such as thiarubrine A (3) and B (4)

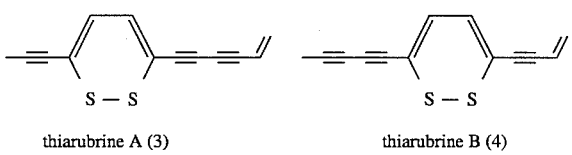

are extremely toxic, but they also exhibit a wide spectrum of biological activity, including antiviral and antibiotic activities (Towers, G. H. N. et al. *Planta Medica* 1985, 3,225–229, incorporated herein by reference). Thiarubrine compounds are known for their useful antifungal and bacteriocidal properties from U.S. Pat. No. 5,202,348 dated Apr. 13, 1993, incorporated herein by reference. The compounds are light sensitive and need to be used and stored in the dark. While the modes of biological activities of these polyacetylene-1,2-dithiins remain uncertain, it has been suggested that the 1,2-dithiin heterocycle portion of these natural products is responsible for their characteristic biological properties (Constabel, C. P.; Towers, G. H. N., *Planta Medica* 1989, 55, 35–37). In addition, since the presence of polyacetylenic functional groups is well known to cause adverse cytotoxicity (Towers, G. H. N.; Champagne, D. B. In *Chemistry and Biology of Naturally-occurring Acetylenes and Related Compounds* (NOARC), ed by Lam, J. et al. Elsevier, Amsterdam, 1988, 139–149), considerable synthetic efforts have been devoted to the synthesis of the 1,2-dithiin heterocycle exclusive of any acetylenic functionality (Freeman, E. et al. *Sulfur Reports* 1989, 9, 207–246). Approaches reported in both the first synthesis of 1,2-dithiin molecules (Schroth, W. et al. *Angew. Chem. Int.Ed.Engl.* 1967,6, 698–699) and a recent improved synthesis (Koreeda, M. and Yang, W. *Synlett.* 1994, 201–203, incorporated herein by reference) commence with the stereo- and regioselective formation of bis-sulfide 6 by the addition of a benzylthioate anion to 1,4-disubstituted 1,3-butadiyne 5, in a series of steps as follows:

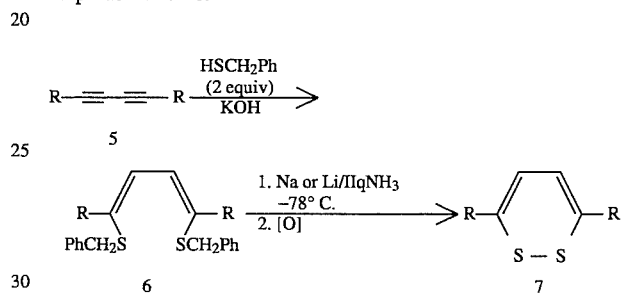

where R represents Ph, H, CH$_2$OH or C≡CH. Reductive removal of the benzyl group of the key intermediate 6 under dissolving metal conditions in liquid ammonia and subsequent oxidative disulfide bond formation provide 1,2-dithiins 7. Although these 1,2-dithiin-containing molecules hold great promise for medicinal applications, their use as efficacious medicines may be severely limited due to their water insolubility.

DETAILED DESCRIPTION OF THE INVENTION

The invention in one preferred aspect is directed to novel, water-soluble glycosylated derivatives of 3,6-bis(hydroxymethyl)-1,2-dithiin of the formula 8

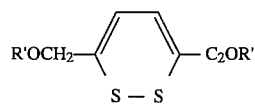

where R' represents a moiety selected from mono and disaccharides 8A–8D as follows, each having the 2,3-dideoxyhex-2-enopyranoside moiety:

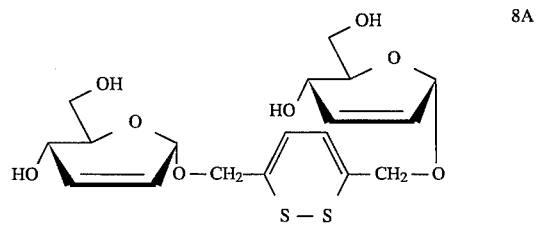

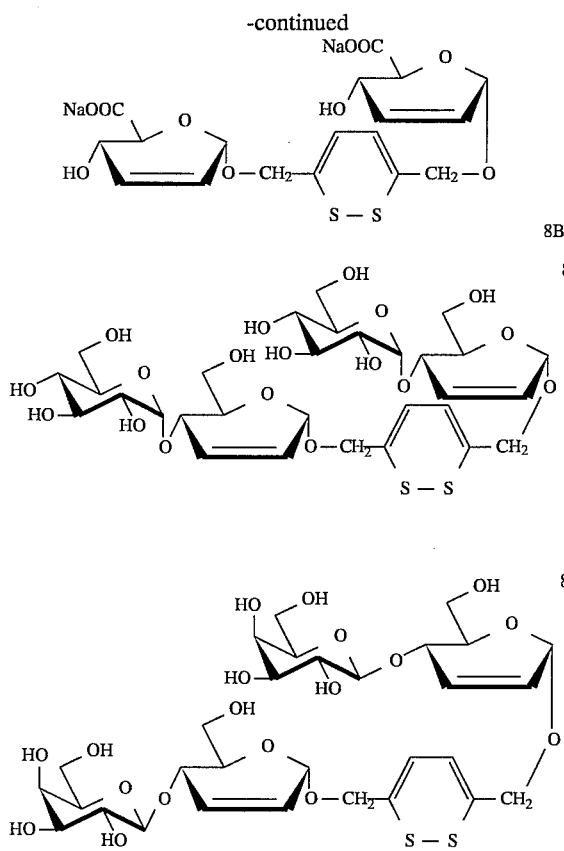

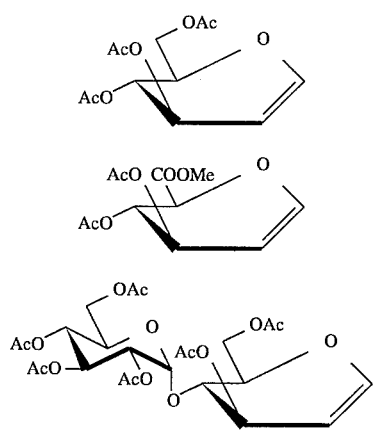

The invention in another preferred aspect comprises the synthesis of these glycosylated 1,2-dithiin derivatives through 1) a novel and highly efficient iodine-catalyzed glycosylation of 3,6-bis(hydroxymethyl)-1,2-dithiin (8; R=H) with the respective peracetylated glycals: triacetyl-D-glucal (9A) (purchased from the Aldrich Chemical Company, Milwaukee, Wis.), D-arabinohex-1-enopyranosyluronate (9B) (Wyss, P. C. et al., *Hel. Chim. Acta* 1975, 58, 1847–1864, hexaacetyl D-maltal (9C) (Haworth, W. N. et al. *J. Chem. Soc.* 1934, 302–303), and hexaacetyl D-lactal (9D) (Haskins, W. T. et al. *J.Am. Chem. Soc.* 1942, 64, 1852–1856), having the following structures:

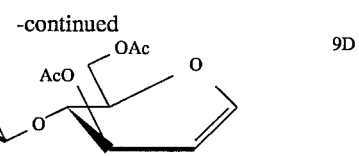

and 2) mild-base hydrolysis thereof to afford their respective free-polyhydroxy, water-soluble derivatives 8A, 8B, 8C, and 8D.

The invention comprises several novel protocols for the synthesis of the 1,2-dithiin anti-aromatic heterocycle. One method involves the regio- and stereoselective bis-addition of 2-(trimethylsilyl)ethanethiol onto 1,4-disubstituted 1,3-butadiyne 5 in the presence of a catalytic amount of KOH. Treatment of the resulting bis-thiol adduct 10 with tetra(n-butyl)ammonium fluoride followed by oxidative disulfide bond formation through the use of the oxidant iodine in a one-pot operation results in the smooth formation of the desired 1,2-dithiin 11, by the following Scheme 1:

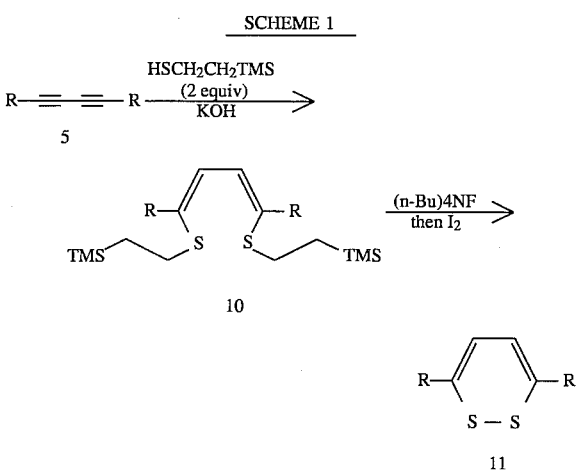

where R has the above significance.

This novel protocol is significantly advantageous to the above-mentioned existing methods in both efficiency and simplicity of operation. Of particular significance in the context of practical application is the fact that the present invention does not require the use of low-temperature dissolving metal reduction in liquid ammonia. This obviates not only the need for the often-laborious efforts to maintain the required low temperatures, but also the additional costs incurred in connection with the safe disposal of a large volume of ammonia.

Another preferred method comprises the synthesis of 3,6-bis(hydroxymethyl)-1,2-dithiin (14) and its glycosylation with hexaacetyl D-maltal (9C) to give rise to, upon hydrolysis of the acetyl groups, bis-disaccharide appended 3,6-bis(hydroxymethyl)-1,2-dithiin (8C), by the following Scheme 2:

SCHEME 2

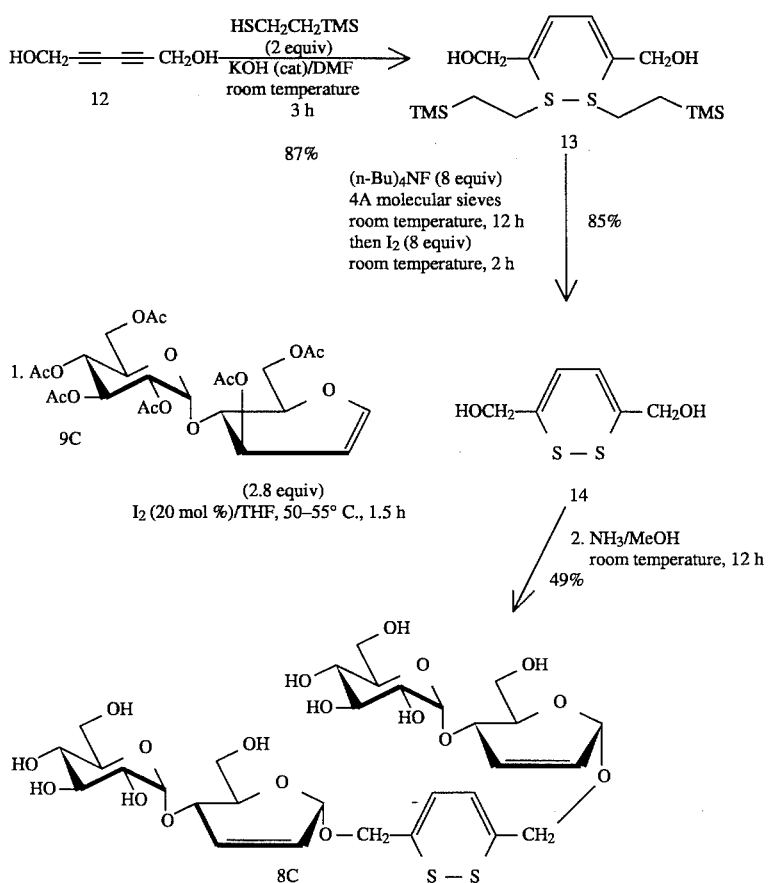

Bis-disaccharide derivatives such as 8C and 8D are highly water-soluble and appear ideally suited for the delivery of the 1,2-dithiin-based drugs to the targeted organs/tissues due to the relatively facile hydrolysis of these glycosylated derivatives to 3,6-bis(hydroxymethyl)-1,2-dithiin (14) even under pH 5 (Stache, U. et al. *Agnew. Chem. Int.Ed. Engl.* 1982, 21, 547).

The derivatives according to the invention have useful antifungal and antibacterial activity in dosage form for mammals, e.g. for topical or other suitable application, in a pharmaceutically acceptable carrier such as water, physiological saline, or other carrier. A composition dosage form containing the derivative can be used, e.g., in a concentration of about 1 to 100 nanograms/mL, to control *E. coli, S. aureus, C. albicans*, and the like, with activity comparable to that of the thiarubrines A and B.

In another preferred method, the glycosylated 1,2-dithiin derivatives can be readily accessed without construction of the light-sensitive, acid-labile 1,2-dithiin heterocycle in an early stage of the synthesis. Thus, the invention comprises an alternate synthesis of these glycosylated 1,2-dithiins (8A, 8B, 8C and 8D), by the following Scheme 3:

SCHEME 3

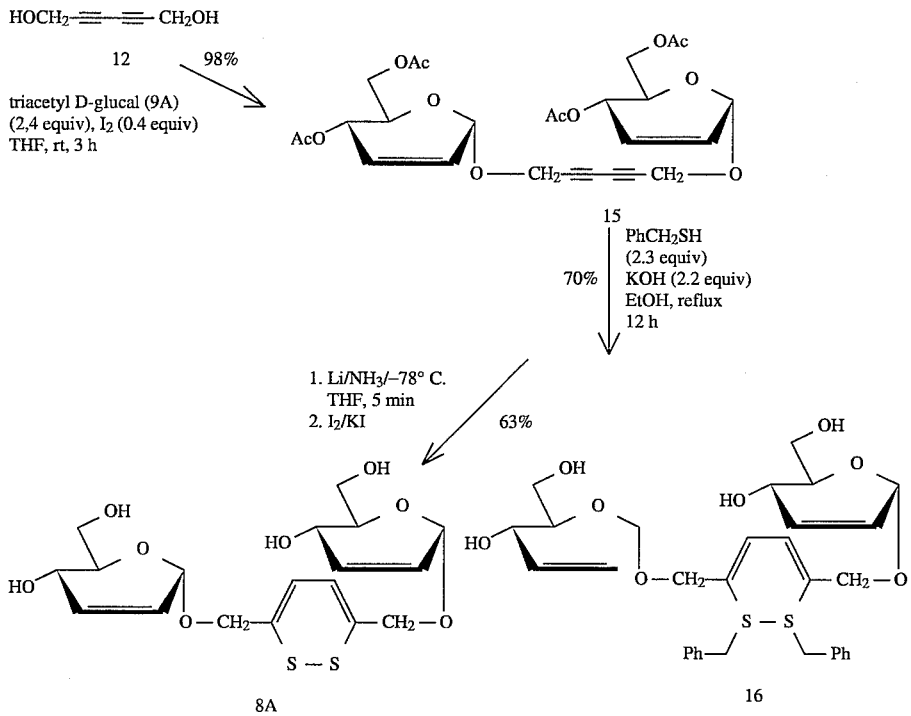

This synthesis involves the use of the iodine-catalyzed glycosylation as the first step in the synthesis followed by the addition of two molecules of a protected thiol to produce 16. Bis-thiol adduct 16 can be effectively converted into the glycosylated 1,2-dithiin 8A in 63% overall yield involving dissolving-metal reduction and subsequent oxidative cyclization with iodine. A salient feature of this overall highly efficient method for the synthesis of the glycosylated 1,2-dithiins over the above-mentioned method that involves the glycosylation of 3,6-bis(hydroxymethyl)-1,2-dithiin (14) lies in the fact that the construction of the labile 1,2-dithiin heterocycle is accomplished as the last step of the synthesis.

The following examples describe preferred embodiments of the invention and also describe the best mode of carrying out the same.

EXAMPLE 1

(Z,Z)-2,5-Bis[β-(trimethylsilyl)ethylthio]-2,4-hexadiene-1,6-diol (13)

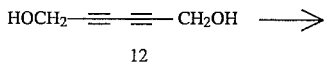
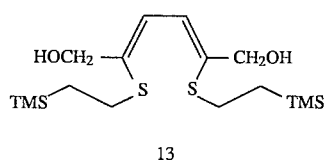

2-(Trimethylsilyl)ethanethiol (336 μL, 2.10 mmol) was added to a suspension of 300 mg of KOH in 3 mL of DMF. After stirring at room temperature for 20 minutes, 110 mg of 1,6-dihydroxy-2,4-hexadyne (12) (1.00 mmol) was added to the mixture. The resulting mixture, which turned immediately brownish, was stirred at room temperature for 3 hours, upon which time it was poured into 40 mL of a 1:1 water/ether mixture. The ether layer was separated and the aqueous layer was extracted again with 20 mL of ether. The combined ether layers were washed first with water (25 mL) and then with brine (30 mL) and dried over anhydrous $MgSO_4$. The crude reaction mixture obtained by removal of the solvent by rotary evaporation was purified by silica gel flash column chromatography using 3:1 ethyl acetate/hexanes as the eluent, affording 328 mg of the bis-thiol adduct 13 (87%) as a white solid: mp 64.5°–65.0° C. (hexanes); $R_f$ 0.59 (1:3 ethyl acetate/hexanes); $^1H$ NMR (360 MHz, $CDCl_3$) δ0.01 (s,18H), 0.82–0.87 (4H) and 2.75–2.80 (4H) (two sets of identical AA'XX' spin systems), 1.90 (s,2H), 4.27 (s,4H), 6.89 (s, 2H); $^{13}C$ NMR (90 MHz, $CDCl_3$) δ-1.81 (q, 6C), 18.06 (t, 2C), 27.80 (t, 2C), 65.87 (t, 2C), 127.78 (d, 2C), 138.73 (s,2C); IR (KBr) 3349 (s), 3026 (w), 1612 (w), 1559 (w), 1414 (m), 1249 (s), 1031 (s) 859 (s) $cm^{-1}$. Anal. Calcd for $C_{16}H_{34}O_2S_2Si_2$: C, 50.74; H, 9.05. Found: C, 50.47; H, 8.91.

3,6-Bis(hydroxymethyl)-1,2-dithiin (14)

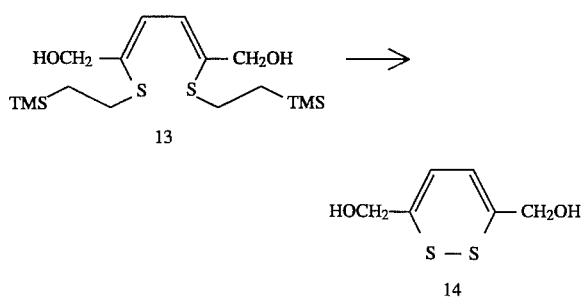

To 5 mL of dry THF containing 100 mg of 4 Å molecular sieves was added 800 µL of 1M tetra (n-butyl) ammonium fluoride in THF (0.800 mmol) at room temperature and the mixture was stirred at that temperature for several minutes and then was treated with 37.9 mg (0.100 mmol) of bis-thiol adduct 13. The resulting mixture was stirred at room temperature overnight, at which point 200 mg of iodine (0.788 mmol) in 0.5 mL of THF was added and the reaction mixture was stirred at room temperature for 2 hours. The reaction mixture was then diluted with 20 mL of ether and the resulting mixture was washed first with 0.1M aqueous $Na_2S_2O_3$ (15 mL) and then with brine (15 mL). The organic layer thus obtained was dried over anhydrous $Na_2SO_4$ and the solvent was removed by rotary evaporation. The resulting crude solid residue was purified by silica gel flash column chromatography with ethyl acetate/hexanes (2:1) as the eluent to afford 15.0 mg of 3,6-bis (hydroxymethyl)-1,2-dithiin (14) (85%) as a red-colored solid. The spectral characteristics were identical to those previously reported (Koreeda, M. and Yang, W. *Synlett.* 1994, 201–203).

3,6-Di[4,6-di-O-acetyl-2,3-dideoxy-α-D-erythro-hex-2-enopyranosyl]oxymethyl-1,2-dithiin (17A)

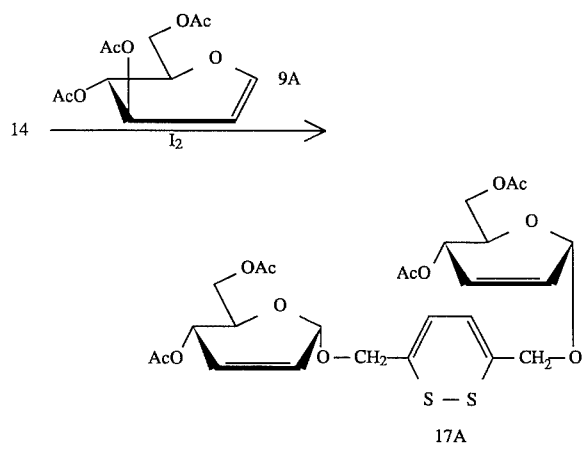

To a solution of 17.6 mg of 3,6-bis (hydroxymethyl)-1, 2-dithiin (14) (0.100 mmol) and 57.2 mg of triacetyl-D-glucal (0.210 mmol) in 5 mL of dry THF was added 5.1 mg of iodine (20 mol %) at room temperature. The resulting mixture was warmed to 50° C. and was stirred at that temperature for 1.5 hours, upon which time the solution was cooled to room temperature and diluted with 20 mL of ether. The resulting mixture was washed first with 15 mL of 0.1M aqueous $Na_2S_2O_3$ (15 mL) and then with brine (15 mL), and dried over anhydrous $MgSO_4$. The solvent was removed by rotary evaporation and the resulting crude residue was purified by silica gel flash column chromatography using 3:2 ethyl acetate/hexanes 3:2 as the eluent to provide 54.1 mg of the bis-glycosylated dithiin 17A (90%) as an orange crystalline solid: mp 96°–99° C.; $R_f$ 0.37 (3:2 ethyl acetate/hexanes); $[α]_D^{20}$+115.2° (C=1.03, $CHCl_3$); $^1H$ NMR (360 MHz, $CDCl_3$) δ2.09 (s,6H), 2.11 (s,6H), 4.10–4.16 (m, 2H), 4.21 (2H) and 4.27 (2H) (two sets of identical AB spin systems, $J_{AB}$=12.2 Hz; each of the 4.21 and 4.27 ppm peaks is further split into d with J=2.5 and 4.9 Hz, respectively), 4.27 (2H) and 4.40 (2H) (two sets of identical AB spin systems, $J_{AB}$=13.0 Hz), 4.33 (2H) and 5.89 (2H) (two sets of identical AB spin systems, $J_{AB}$=9.3 Hz), 5.11 (dd, 2H, J=2.7, 1.3 Hz), 5.34 (dddd, 2H, J=9.6, 1.9, 1.6, 1.3 Hz), 5.84 (2H) and 5.93 (2H) [(two sets of identical AB spin systems, $J_{AB}$=10.2 Hz; each of the 5.84 and 5.93 ppm peaks is further split into dd (J=2.7, 1.9 Hz) and d (J=1.6 Hz), respectively], 6.36 (s, 2H); $^{13}C$ NMR (90 MHz, $CDCl_3$) δ20.84 (q, 2C), 20.98 (q, 2C), 62.75 (t, 2C), 65.06 (d, 2C), 67.26 (d, 2C), 69.68 (t, 2C), 93.49 (d, 2C), 126.86 (d, 2C), 127.17 (d, 2C), 129.73 (d,2C), 131.99 (s,2C), 170.26 (s, 2C), 170.77 (s, 2C); IR (neat) 2923 (m), 2907 (m), 1736 (s), 1371 (s), 1230 (s), 1050 (s), 1023 (s) $cm^{-1}$. Anal. Calcd for $C_{26}H_{32}O_{12}S_2$: C, 51.99; H, 5.37. Found: C, 51.56; H, 5.37.

3,6-Di[2,3-dideoxy-α-D-erythro-hex-2-enopyranosyl]oxymethyl-1,2-dithiin (8A)

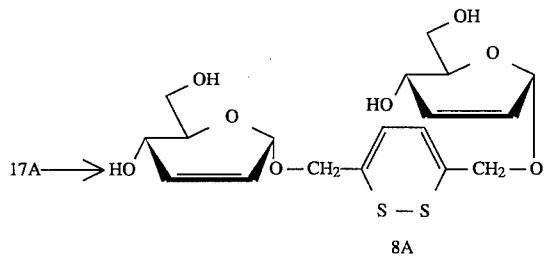

Tetraacetate 17A (20.0 mg) dissolved in 1 mL of methanol was treated with 1 mL of 0.1M aqueous $Ba(OH)_2$ and the resulting solution was stirred at room temperature for 1 hour, upon which time the hydrolyzed product was extracted with 4:1 $CHCl_3$/n-BuOH (3×50 mL). The combined organic layers were dried over anhydrous $MgSO_4$ and the solvent was removed by rotary evaporation. The resulting crude product was purified by silica gel flash column chromatography using 4:1 $CHCl_3$/MeOH as the eluent to afford 12.3 mg of tetraol 8A (85%) as a yellow solid: mp 239°–240° C. ($CHCl_3$/acetone); $R_f$ 0.40 (4:1 $CHCl_3$/MeOH); $[α]_D^{20}$+ 151.4° (c=1.01, MeOH); $^1H$ NMR (360 MHz, acetone-$d_6$) δ2.82 (t,2H, J=1.0 Hz; 2×$CH_2OH$), 3.67–3.70 (m, 2H), 3.68 (2H) and 3.82 (2H) (two sets of identical AB spin systems, $J_{AB}$=9.7 Hz), 4.06 (ddd, 2H, J=7.6, 2.1, 1.6 Hz), 4.18 (d, 2H, J=6.6 Hz; CHOH), 4.28 (2H) and 4.41 (2H) (two sets of identical AB spin systems, $J_{AB}$=13.0 Hz), 5.04 (dd,2H, J=2.7, 1.2 Hz), 5.71 (2H) and 5.94 (2H) (two sets of identical AB spin systems, $J_{AB}$=10.0 Hz, each of the 5.71 and 5.94 ppm peaks is further split into dd with J=2.7, 2.1 and 1.6, 1.2 Hz, respectively), 6.46 (s, 2H); $^{13}C$ NMR (acetone-$d_6$; 90 MHz) δ62.68 (t, 2C), 64.15 (d, 2C), 69.94 (d, 2C), 73.68 (t, 2C), 94.15 (d, 2C), 126.03 (d, 2C), 127.50 (d, 2C), 133.01 (s, 2C), 135.52 (d, 2C); IR (KBr) 3416 (s), 3300–3200 (br s), 3045 (w), 2941 (m), 1654 (w), 1591 (w), 1404 (m), 1044 (s) cm$^{-1}$. Anal. Calcd for $C_{18}H_{24}O_8S_2$: C, 49.99; H, 5.59. Found: C, 49.87; H, 5.72.

By the above procedure for glycosylation of 3,6-bis(hydroxymethyl)-1,2-dithiin but using methyl 3,4-diacetyl-1,2-dideoxy-D-arabinohexenopyranosyluronate instead of triacetyl D-glucal, the product obtained after work-up is 3,6-di[methyl 4-O-acetyl-2,3-dideoxy-α-D-erythro-hex-2-enopyranosyluronate]oxymethyl-1,2-dithiin (17B). This diacetate dimethyl ester (20 mg) dissolved in 1 mL of THF is treated with 3 mL of 0.1M aqueous NaOH, and the resulting solution is stirred at room temperature for three hours. The hydrolyzed product is extracted, the extract layers are combined and dried, and the solvent removed. After purification by silica gel chromatography, the product is 3,6-di[sodium 2,3-dideoxy-α-D-erythro-hex-2-enopyranosyluronate]oxymethyl-1,2-dithiin (8B).

EXAMPLE 2

3,6-Di-[6-O-acetyl-4-O-(2,3,4,6-tetra-O-acetyl-α-D-glucopyranosyl)-2,3-dideoxy-α-D-erythro-hex-2-enopyranosyl]oxymethyl-1,2-dithiin (17C)

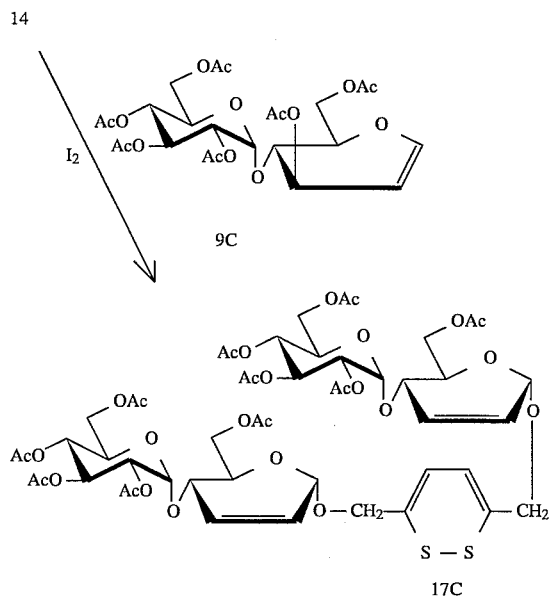

To a solution of 44.1 mg of 3,6-bis(hydroxymethyl)-1,2-dithiin (14) (0.251 mmol) and 397 mg of hexaacetyl D-maltal (9C) (0.707 mmol) in 10 mL of THF was added 25.3 mg of iodine (0.100 mmol). The reaction mixture was heated to 50°–55° C. for 15 hours and then was cooled to room temperature and was diluted with ether (25 mL). The resulting mixture was washed first with 0.1M aqueous $NaS_2O_3$ (10 mL) and then with brine (15 mL). The organic layer was dried over anhydrous $MgSO_4$ and the solvent was removed by rotary evaporation. The resulting crude oil was purified by silica gel flash column chromatography using 3:1 ethyl acetate/hexanes as the eluent to afford 294 mg of decaacetate 17C (98%) as an orange solid: mp 50°–59° C.; $R_f$ 0.51 (3:1 ethyl acetate/hexanes); $[α]_D^{20}$+152.3° C. (c=1.02, CHCl$_3$); $^1$H NMR (360 MHz, CDCl$_3$) δ1.95 (s,6H), 1.97 (s,6H), 2.01 (s,6H), 2.03 (s,6H), 2.06 (s,6H), 3.98–4.06 (m, 6H), 4.17–4.34 (m, 12H), 4.77 (dd, 2H, J=10.3, 3.9 Hz), 5.00 (dd,2H, J=9.8, 9.8 Hz), 5.01 (s,2H), 5.24 (d, 2H, J=3.9 Hz), 5.34 (dd,2H, J=10.3, 9.8 Hz), 5.77 (2H) and 5.82 (2H) (two sets of identical AB spin systems, $J_{AB}$=10.4 Hz), 6.32 (s,2H); $^{13}$C NMR (90 MHz, CDCl$_3$) δ20.58 (q, 4C), 20.66 (q, 4C), 20.85 (q, 2C), 61.62 (t, 2C), 63.14 (t, 2C), 67.69 (d, 2C), 68.14 (d, 4C), 69.56 (d, 2C), 69.78 (d, 2C), 70.71 (d,2C), 93.27 (d,2C), 94.06 (d,2C), 126.95 (d,2C), 127.29 (d,2C), 128.99 (d,2C), 131.92 (s,2C), 169.54 (s,2C), 169.96 (s,2C), 170.25 (s,2C), 170.56 (s,4C); IR (KBr) 2963 (w), 1749 (s), 1438 (w), 1368 (m), 1228 (s), 1137 (w), 1032 (s) cm$^{-1}$.

3,6-Di[4-O-(α-D-glucopyranosyl)-2,3-dideoxy-α-D-erythrohex-2-enopyranosyl] oxymethyl-1,2-dithiin (8C)

17C ⟶

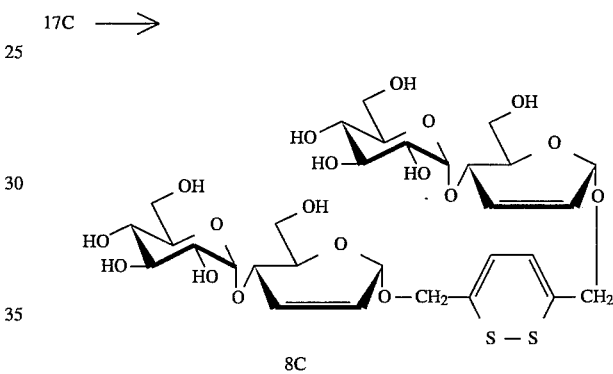

Ammonia was introduced to a cooled (0° C.) solution of 2.50 g of decaacetate 17C (2.13 mmol) in 50 mL of MeOH until the solution became saturated with ammonia (total of about 8.5 g of ammonia). The mixture was warmed up to room temperature and stirred overnight. Removal of ammonia and MeOH by rotary evaporation provided a viscous, red oil, which was purified by silica gel flash column chromatography using 1:1 ethyl acetate/MeOH as the eluent to afford 811 mg (50%) of the glycosylated dithiin 8C as pure orange crystals (residual acetamide was removed by trituration of the crystals with CHCl$_3$): mp 142°–144° C.; $R_f$ 0.43 (1:1 ethyl acetate/MeOH); $[α]_D^{20}$+153.6° cc=1.03 H$_2$O); $^1$H NMR (360 MHz, D$_2$O) δ3.44 (dd, 2H, J=9.1, 9.1 Hz), 3.56–4.00 (m, 18H), 4.35–4.48 (m, 4H), 5.20 (br d, 4H, J=7.0 Hz), 5.94 (br d, 2H, J=10.0 Hz), 6.24 (br d, 2H, J=10.0 Hz), 6.55 (s,2H); $^{13}$C NMR (90 MHz, D$_2$O) δ63.23 (t, 2C), 63.60 (t, 2C), 70.19 (d, 2C), 72.21 (d, 2C), 72.54 (t,2C), 73.01 (d, 2C), 73.82 (d, 2C), 75.44 (d, 2C), 75.64 (d, 2C), 96.43 (d, 2C), 98.89 (d, 2C), 128.79 (d, 2C), 131.54 (d, 2C), 132.92 (d, 2C), 134.50 (s,2C); IR (KBr) 3395 (s,br), 2921 (m), 1664 (w), 1451 (m), 1403 (m), 1142 (m), 1101 (m), 1026 (s).

EXAMPLE 3

3,6-Di[6-O-acetyl-4-O-(2,3,4,6-tetra-O-acetyl-β-D-galactopyranosyl)-2,3-dideoxy-α-D-erythro-hex-2-enopyranosyl]oxymethyl-1,2-dithiin (17D)

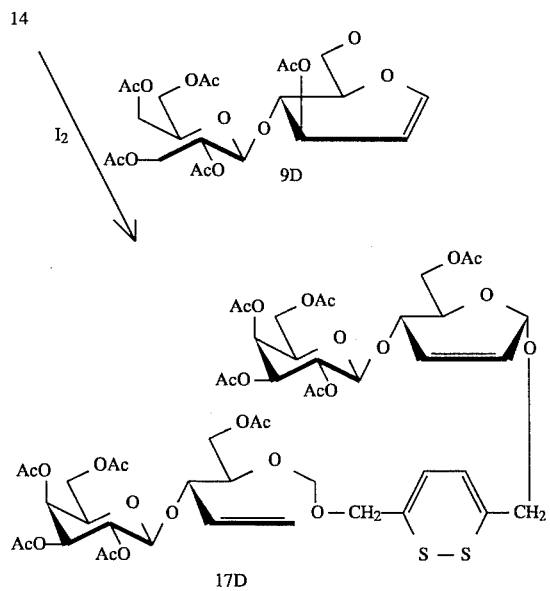

To a solution of 100 mg of 3,6-bis (hydroxymethyl)-1,2-dithiin (14) (0.57 mmol) and 700 mg of hexaacetyl D-lactal (9D) (1.25 mmol) in 5 mL of dry THF was added 29.0 mg of iodine (0.11 mmol). The reaction mixture was stirred at room temperature for 3 hours, at which point it was diluted with ether (25 mL). The resulting mixture was washed successively with 0.1M aqueous $Na_2S_2O_3$ (15 mL), water (20 mL), and brine (20 mL), and dried over anhydrous $MgSO_4$. Removal of the solvent by rotary evaporation gave a viscous, red oil, which was purified by silica gel flash column chromatography using ether as the eluent to afford 430 mg (>98%) of decaacetyl dithiin derivative 17D as an orange, crystalline solid: mp 89°–95° C.; $R_f$ 0.34 (3:1 ethyl acetate/hexanes); $[\alpha]_D^{20}$+ 64.2° (c=1.04, $CHCl_3$); $^1H$ NMR (360 MHz, $CDCl_3$) δ1.98 (s, 6H), 2.05 (s, 6H), 2.08 (s, 6H), 2.13 (s, 6H), 2.16 (s, 6H), 3.92 (dd, 2H, J=6.9, 6.5 Hz), 4.01–4.39 (m, 18H), 4.57 (d, 2H, J=7.9 Hz), 5.00 (dd, 2H, J=10.4, 3.4 Hz), 5.06 (br s,2H), 5.21 (dd, 2H, J=10.4, 7.9 Hz), 5.38 (d,2H, J=2.6 Hz), 5.76 (2H) and 6.13 (2H) (two sets of identical AB spin systems, $J_{AB}$=10.4 Hz; each of the 5.76 ppm peaks is further split into dd with J=2.5, 2.0 Hz), 6.34 (s,2H); $^{13}C$ NMR (90 MHz, $CDCl_3$) δ20.55 (q, 6C), 20.66 (q,2C), 20.91 (q, 2C), 61.26 (t,2C), 62.88 (t, 2C), 66.84 (d, 2C), 67.75 (d, 2C), 68.76 (d, 2C), 69.43 (t,2C), 70.74 (d,2C), 70.82 (d, 2C), 73.24 (d,2C), 93.39 (d,2C), 102.28 (d, 2C), 126.50 (d, 2C), 126.67 (d,2C), 131.84 (s,2C), 131.94 (d, 2C), 169.39 (s,2C), 170.09 (s,2C), 170.24 (s,2C), 170.36 (s,2C), 170.70 (s,2C); IR (KBr) 2924 (w), 1751 (s), 1370 (m), 1225 (s,br), 1046 (s,br) cm$^{-1}$. Anal. Calcd for $C_{50}H_{64}O_{28}S_2$: C, 51.02; H, 5.48. Found: C, 51.01; H, 5.63.

3,6-Di[4-O-(β-D-galactopyranosyl)-2,3-dideoxy-α-D-erythro-hex-2-enopyranosyl]oxymethyl-1,2-dithiin (8D)

17D →

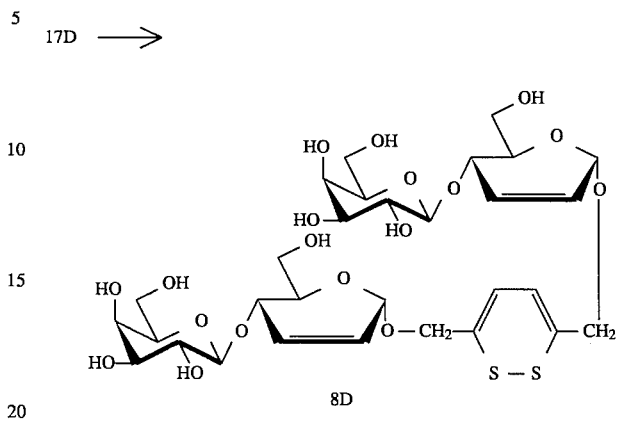

Ammonia was introduced to a solution of 502 mg of decaacetate 17D (0.425 mmol) in 15 mL of MeOH at 0° C. until the solution became saturated with ammonia (total of about 2.3 g of ammonia). The mixture was then warmed up to room temperature and stirred at that temperature overnight. Removal of ammonia and MeOH by rotary evaporation gave a viscous, red oil which was dissolved in 1 mL of MeOH. To this MeOH solution was added 15 mL of ether, which provided the hydrolyzed product 8D as orange precipitates. A total of 307 mg (95%) of 8D was obtained after repeating this dissolution-precipitation sequence several times: mp 139°– 142° C.; $R_f$ 0.41 (1:1MeOH/ethyl acetate); $[\alpha]_D^{20}$+77.6° (c=1.03, $H_2O$); $^1H$ NMR (360 MHz, $D_2O$) δ3.53 (dd, 2H, J=9.9, 7.8 Hz), 3.64–3.98 (m, 18H), 4.39–4.49 (m, 4H), 4.51 (d,2H, J=7.8 Hz), 5.23 (br s,2H), 5.89 (2H) and 6.24 (2H) (two sets of identical AB spin systems, $J_{AB}$=10.3 Hz; each of the 5.89 ppm peaks is further split into dd with J=2.6, 2.1 Hz), 6.55 (s,2H); $^{13}C$ NMR (90 MHz, $D_2O$) δ63.17 (t,2C), 63.65 (t, 2C), 71.28 (d, 2C), 72.54 (t, 2C), 73.19 (d, 2C), 73.64 (d, 2C), 74.66 (d, 2C), 75.39 (d, 2C), 77.89 (d, 2C), 96.25 (d, 2C), 106.30 (d,2C), 128.75 (d,2C), 131.46 (d,2C), 134.45 (s,2C), 135.56 (d,2C); IR (KBr) 3396 (s,br), 2900 (m), 1664 (w), 1442 (m), 1394 (m), 1141 (s), 1031 (s) cm$^{-1}$.

EXAMPLE 4

1,6-Di[4,6-di-O-acetyl-2,3-dideoxy-α-D-erythro-hex-2-enopyranosyl]oxy-2,4-hexadiyne (15)

$HOCH_2$—≡≡—$CH_2OH$  $\xrightarrow{9A}{I_2}$

12

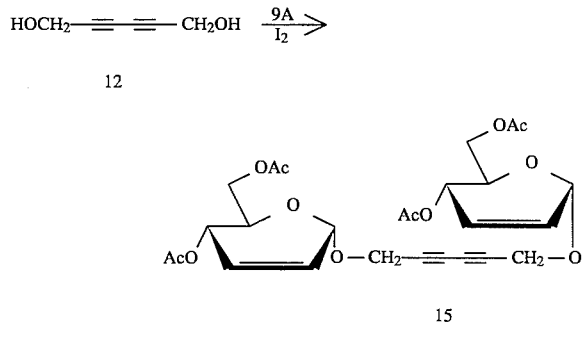

15

To a solution of 101 mg of 1,6-dihydroxy-2,4-hexadiyne (12) (1.00 mmol) and 653 mg of triacetyl D-glucal (9A) (2.40 mmol) in 15 mL of THF was added 101 mg of iodine (0.40 mmol). The reaction mixture was stirred at room temperature for 3 hours, at which time it was diluted with ether (25 mL). The resulting solution was washed successively with 0.1M aqueous $Na_2S_2O_3$ (15 mL), water (20 mL), and brine (20 mL), and dried over anhydrous $MgSO_4$. Removal of the solvent by rotary evaporation provided a viscous, slightly yellow oil, which was purified by silica gel flash column chromatography using 1:1 ethyl acetate/hexanes as the eluent to afford 534 mg (>98%) of the glycosylated product 15 as a colorless liquid; $R_f$ 0.15 (1:1 ethyl acetate/hexanes); $[\alpha]_D^{20}$+ 157.0° (c=1.11, $CHCl_3$); $^1H$ NMR (360 MHz, $CDCl_3$) δ2.09 (s,6H), 2.11 (s,6H), 4.07 (ddd, 2H, J=9.7, 5.1, 2.4 Hz), 4.18 (2H) and 4.26 (2H) (two sets of identical AB spin systems, $J_{AB}$=12.2 Hz; each of the 4.18 and 4.26 ppm peaks is further split into d with J=2.4 and 5.1 Hz, respectively), 4.39 (d,4H,J=3.0 Hz), 5.21 (m, 2H), 5.34 (ddd, 2H, J=9.7, 1.6, 1.4 Hz), 5.84 (2H) and 5.95 (2H) [two sets of identical AB spin systems, $J_{AB}$=10.2 Hz; each of the 5.84 and 5.95 ppm peaks is further split into dd (J=1.6, 1.4 Hz) and d (J=1.4 Hz), respectively]; $^{13}C$ NMR (90 MHz, $CDCl_3$) δ20.61 (q,2C), 20.76 (q,2C), 55.31 (t,2C), 62.51 (t, 2C), 64.88 (d, 2C), 67.08 (d, 2C), 70.29 (s, 2C), 74.88 (s,2C), 92.79 (d,2C), 126.86 (d,2C), 129.76 (d,2C), 170.00 (s,2C), 170.50 (s,2C); IR (neat) 2911 (m), 1747 (s), 1444 (m), 1374 (m), 1241 (s), 758 (m) $cm^{-1}$.

(Z, Z)-1,6-Di[4,6-di-O-acetyl-2,3-dideoxy-α-D-erythro-hex-2-enopyranosyl] oxy-2,5-dibenzylthio-2,4-hexadiene (16)

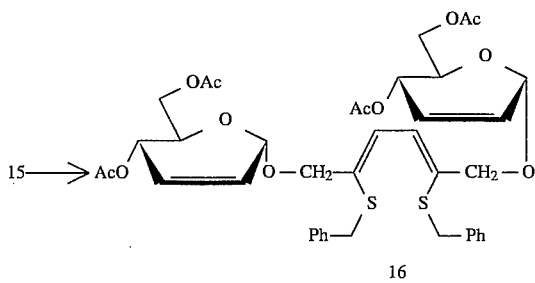

Benzyl mercaptan (377 μL, 3.21 mmol) was added to a suspension of KOH (172 mg, 3.07 mmol) in absolute EtOH (30 mL). The mixture was heated to reflux, upon which time tetraacetate 15 (746 mg, 1.40 mmol) in EtOH (enough to dissolve the tetraacetate 15, ca 0.5 mL) was added. The solution which turned immediately brownish was refluxed for 12 hours. The reaction mixture was cooled to room temperature and the solvent was removed by rotary evaporation. The dark-brown residue thus obtained was purified by silica gel flash column chromatography using 1:5MeOH/$CHCl_3$ as the eluent, providing 600 mg of bis-thiol adduct 16 (70%) as a white solid: mp 69.5°–72.5° C. ($CHCl_3$); $R_f$ 0.36 (4:1 $CHCl_3$/MeOH); $[\alpha]_D^{20}$–25.2° (c=0.97,MeOH); $^1H$ NMR (360 MHz, acetone-$d_6$) δ2.84 (s, 2H), 3.67–3.75 (m, 6H), 4.06 (s,4H), 4.19 (d, 2H, J=6.6 Hz), 4.25 (2H) and 4.43 (2H) (two sets of identical AB spin systems, $J_{AB}$=13.5 Hz), 4.99 (m, 2H), 5.73 (2H) and 5.95 (2H) (two sets of identical AB spin systems, $J_{AB}$=10.2 Hz; each of the 5.73 and 5.95 ppm peaks is further split into dd with J=2.6, 2.2 and 1.3, 1.3 Hz, respectively), 6.88 (s, 2H), 7.21–7.37 (m, 10H); $^{13}C$ NMR (90 MHz, acetone-$d_6$) δ36.92 (t,2C), 63.03 (t, 2C), 64.40 (d, 2C), 71.31 (t, 2C), 73.75 (d, 2C), 93.93 (d,2C), 126.43 (d,2C), 127.90 (d,2C), 128.97 (d,4C), 129.31 (d, 2C), 129.81 (d, 2C), 135.35 (d, 4C), 136.58 (d, 2C), 139.10 (s, 2C); IR (KBr) 3318 (s,br), 3029 (w), 2897 (m), 1601 (w), 1555 (w), 1036 (s), 845 (m), 713 (m), 694 (m) $cm^{-1}$.

3,6-Di[2,3-dideoxy-α-D-erythro-hex-2-enopyranosyl] oxymethyl-1,2-dithiin (8A)

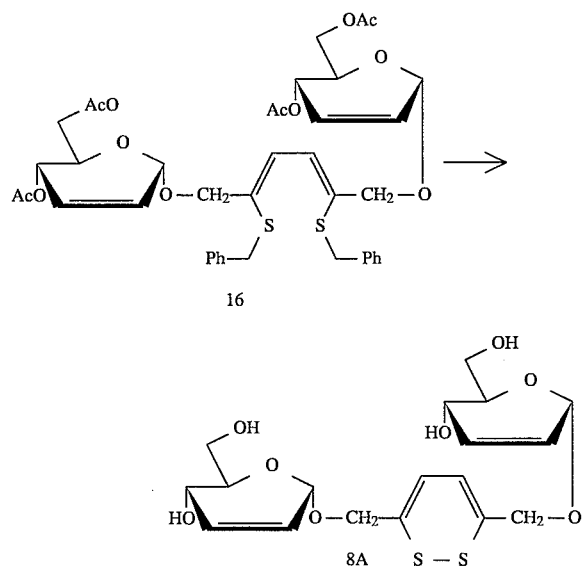

To 10 mL of liquid ammonia cooled to –78° C. were added first lithium (15 mg, 2.16 mmol) and then dry THF (1 mL). After 5 minutes at that temperature, bis-thiol adduct 16 (176 mg, 0.287 mmol) was added to the mixture. The blue color of the Li/ammonia solution disappeared immediately. After 5 minutes, several drops of MeOH were added and the resulting mixture was gradually warmed up to room temperature, during which time most of the ammonia evaporated. The yellow residue thus obtained was then thoroughly mixed, with stirring, with 15 mL of water and 10 mL of ether. The resulting mixture was then cooled to 0° C., and treated dropwise with iodine dissolved in 20% aqueous KI until the red color persisted. To this mixture was added 10 mL of 0.1M aqueous $Na_2S_2O_3$. The aqueous layer was first extracted with ether (15 mL) and then twice with 15 mL each of 4:1 $CHCl_3$/n-BuOH. The combined $CHCl_3$/n-BuOH extracts were dried over anhydrous $MgSO_4$. Removal of the solvent by rotary evaporation followed by drying under vacuum and purification by silica gel flash column chromatography using 1:4MeOH/$CHCl_3$ as the eluent afforded 77.7 mg (63%) of 8A as a red crystalline solid.

Having described the invention, the embodiments of the invention in which an exclusive property or privilege is claimed are defined as follows.

We claim:

1. A water-soluble glycosylated derivative of 3,6-bis (hydroxymethyl)-1,2-dithiin selected from the group consisting of:

A) 3,6-di[2,3-dideoxy-α-D-erythro-hex-2-enopyranosyl] oxymethyl-1,2-dithiin,

B) 3,6-di[sodium 2,3-dideoxy-α-D-erythro-hex-2-enopyranosyluronate] oxymethyl-1,2-dithiin, C) 3,6-di[4-O-(α-D-glucopyranosyl)-2,3-dideoxy-α-D-erythro-hex-2-enopyranosyl] oxymethyl-1,2-dithiin; and D) 3,6-di[4-O-(β-D-galactopyranosyl)-2,3-dideoxy-α-D-erythro-hex-2-enopyranosyl] oxymethyl-1,2-dithiin.

2. The compound of claim 1 having the formula 8A

3. The compound of claim 1 having the formula 8B

4. The compound of claim 1 having the formula 8C

5. The compound of claim 1 having the formula 8D

6. A process for the production of compound A according to claim 1, comprising the steps of glycosylating 3,6-bis(hydroxymethyl)-1,2-dithiin with triacetyl D-glucal to produce the tetraacetate of formula 17A hydrolyzing the tetraacetate to produce compound A, and isolating compound A.

7. A process for the production of compound B according to claim 1, comprising the steps of glycosylating 3,6-bis(hydroxymethyl)-1,2-dithiin with methyl 3,4-diacetyl-1,2-dideoxy-D-arabinohexenopyranosyluronate to produce the tetraacetate of formula 17B hydrolyzing the diacetate dimethyl ester to produce compound B, and isolating compound B.

8. A process for the production of compound C according to claim 1, comprising the steps of glycosylating 3,6-bis(hydroxymethyl)-1,2-dithiin with hexacetyl D-maltal to produce the decaacetate of formula 17C

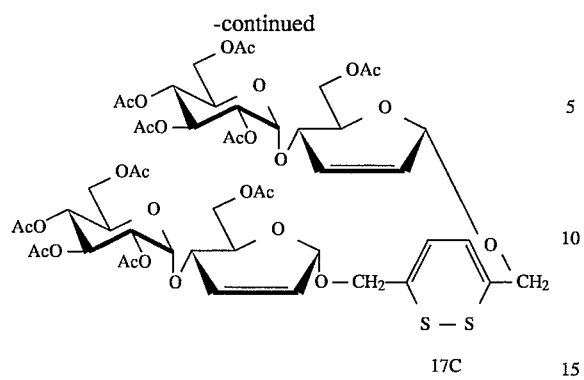

17C hydrolyzing the decaacetate to produce compound C, and isolating compound C.

9. A process for the production of compound D according to claim 1, comprising the steps of glycosylating 3,6-bis(hydroxymethyl)-1,2-dithiin with hexaacetyl D-lactal to produce the decaacetate of formula 17D

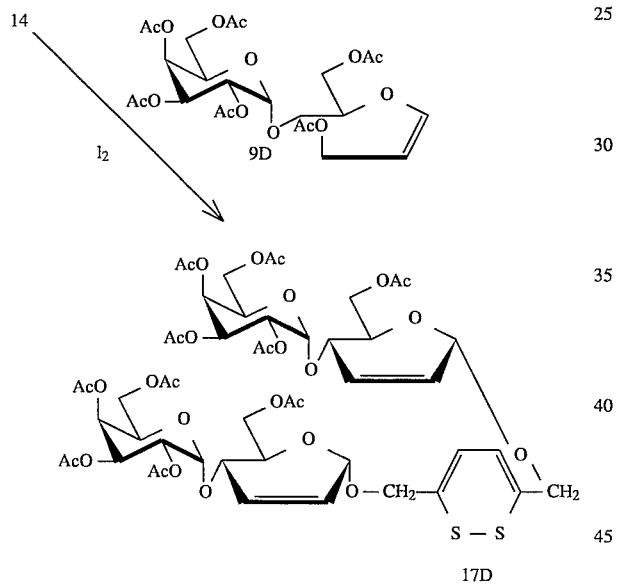

17D hydrolyzing the decaacetate to produce compound D and isolating compound D.

10. A process for the production of compound A according to claim 1, comprising the steps of glycosylating 1,6-dihydroxy-2,4-hexadiyne with triacetyl D-glucal to produce the tetraacetate of formula 15

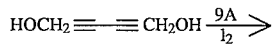

12 reacting the tetraacetate with benzyl mercaptan to produce the bis-thiol adduct of formula 16

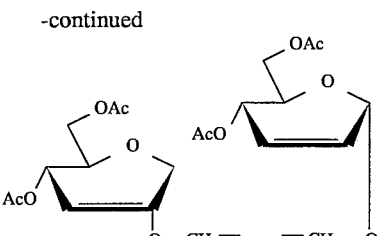

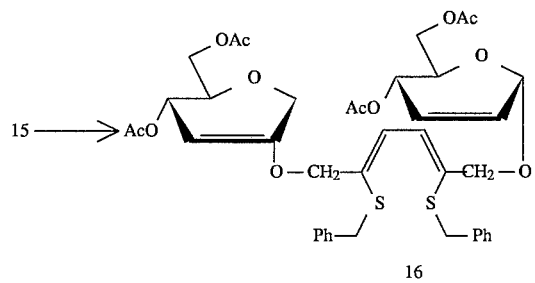

16 reacting the bis-thiol adduct by dissolving metal reduction and oxidative cyclization to produce compound A, and isolating compound A.

11. A process for the production of a 1,2-dithiin having the formula 11

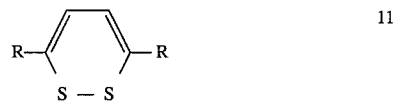

11 where R represents Ph, H, —CH$_2$OH or C≡CH, comprising in steps the bis-addition of 2-(trimethylsilyl)ethanethiol onto 1,4-disubstituted 1,3-butadiyne of formula 5

5 to produce the bis-thiol adduct of formula 10

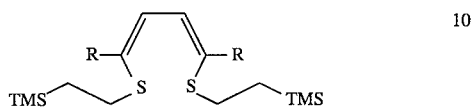

10 treating the resulting bis-thiol adduct with tetra(n-butyl)ammonium fluoride and then causing iodine-oxidative bond formation of the thus treated adduct to produce said 1,2-dithiin.

* * * * *